United States Patent
Bryan et al.

[11] Patent Number: 5,853,456
[45] Date of Patent: Dec. 29, 1998

[54] DEBUBBLING APPARATUS

[76] Inventors: Michael Bryan; Idwal V. Pearson, both of Kodak Limited, Headstone Drive, Harrow, Middlesex, HA1 4TY, United Kingdom

[21] Appl. No.: 875,587
[22] PCT Filed: Dec. 2, 1996
[86] PCT No.: PCT/EP96/05322
   § 371 Date: Jul. 11, 1997
   § 102(e) Date: Jul. 11, 1997
[87] PCT Pub. No.: WO97/20612
   PCT Pub. Date: Jun. 12, 1997

[30] Foreign Application Priority Data

Dec. 6, 1995 [GB] United Kingdom ................ 9524950

[51] Int. Cl.⁶ .................................................. B01D 51/08
[52] U.S. Cl. .................. 95/30; 55/459.1; 96/219
[58] Field of Search ................ 55/277.15, 459.1; 95/30; 96/198, 219; 210/188, 450, 456, 457; 310/316, 317

[56] References Cited

U.S. PATENT DOCUMENTS

| | | |
|---|---|---|
| 2,620,894 | 12/1952 | Peterson et al. . |
| 3,429,743 | 2/1969 | Branson .................................... 95/30 |
| 3,904,392 | 9/1975 | Vaningen et al. .......................... 95/30 |
| 4,612,018 | 9/1986 | Tsuboi et al. ............................... 95/30 |
| 4,806,135 | 2/1989 | Siposs ..................................... 55/459.1 |
| 4,964,984 | 10/1990 | Reeder et al. ........................... 210/188 |
| 5,022,899 | 6/1991 | Hohlfeld et al. ........................... 95/30 |
| 5,236,473 | 8/1993 | Kraus et al. . |
| 5,334,136 | 8/1994 | Schwarz et al. . |
| 5,373,212 | 12/1994 | Beau ...................................... 310/316 |

FOREIGN PATENT DOCUMENTS 2.221.165  11/1974  France .

Primary Examiner—Jay H. Woo
Assistant Examiner—Minh-Chau T. Pham
Attorney, Agent, or Firm—Mark G. Bocchetti

[57] ABSTRACT

Debubbling apparatus may have many uses, for example, in the manufacture of photographic materials where bubbles are to be removed from liquid photographic emulsion prior to application of such emulsion to a supporting substrate, in the food processing industries or in confectionery manufacture where air bubbles are undesirable because they may harbour germs, or in blood transfusion apparatus where air bubbles present a potentially lethal hazard. Described herein is a debubbling apparatus which comprises a vessel having an outlet and an inlet spaced from one another longitudinally of the vessel, means for imparting rotational movement, about a longitudinal axis of the vessel to liquid passed through said vessel from said inlet to said outlet, and means for transmitting a beam of ultrasound along the axis of said vessel in the direction towards said inlet, from a location closer to said outlet than to said inlet.

12 Claims, 4 Drawing Sheets

DEBUBBLING APPARATUS

FIELD OF THE INVENTION

The present invention relates to apparatus for removing bubbles of a gas and/or dissolved gas from a liquid. Such apparatus is herein referred to as "debubbling apparatus".

BACKGROUND OF THE INVENTION

Such debubbling apparatus finds application, for example, in the manufacture of photographic materials, for removing bubbles from liquid photographic emulsion prior to application of such emulsion to a supporting substrate such as paper or plastics film and drying of the emulsion. The invention may also have utility in the food processing industries or in confectionery manufacture, where air bubbles are undesirable because they may harbour germs, or in blood transfusion apparatus, where air bubbles present a potentially lethal hazard.

SUMMARY OF THE INVENTION

It is an object of the present invention to provide an improved debubbling apparatus.

According to one aspect of the present invention, there is provided debubbling apparatus comprising a vessel having an inlet and an outlet spaced apart longitudinally of the vessel, and means for transmitting a beam of ultrasound along a longitudinal axis of the vessel in a direction away from said outlet end and towards the opposite end, and means for maintaining said vessel under positive pressure.

According to another aspect of the present invention, there is provided a method of debubbling a liquid comprising passing the liquid through a vessel from an inlet to an outlet spaced apart longitudinally of the vessel, transmitting a beam of ultrasound along a longitudinal axis of the vessel in a direction away from said outlet and towards said inlet and thereby propelling longitudinally through the vessel, by means of the ultrasonic wind effect, bubbles present in said liquid.

In a preferred embodiment, the debubbling apparatus comprises a vessel having substantial rotational symmetry about a vertical axis, an inlet conduit providing an inlet passage communicating with the interior of said vessel adjacent an upper end thereof and aligned along an axis extending transversely with respect to said vertical axis of the vessel and passing on one side of said vertical axis, whereby the supply of liquid to said vessel via said inlet at a substantial velocity will induce spin of the liquid in the vessel in a predetermined rotational sense about said vertical axis, an outlet for liquid from said vessel communicating with the interior of said vessel via an outlet port in the wall of said vessel adjacent a lower end thereof, a further outlet from said vessel at or adjacent the upper end of the vessel to receive gas, or liquid containing gas bubbles, discharged upwardly through the liquid in said vessel along or close to said vertical axis, and an ultrasonic transmitter mounted in the lower end of said vessel and adapted to transmit ultrasonic energy axially upwardly in said vessel, through liquid in said vessel, towards said further outlet.

The apparatus of the invention makes use of the "ultrasonic wind" effect, a known effect in accordance with which bubbles in a liquid are propelled along an ultrasonic beam in a liquid, away from the source of such beam. The swirl imparted to the liquid within the vessel by the offsetting of the inlet tends to displace any bubbles within the vessel towards the axis of the vessel where they are rapidly conveyed, by the "ultrasonic wind" towards said further outlet. In operation of the apparatus, liquid containing any such bubbles conveyed to said further outlet by the "ultrasonic wind" is withdrawn from the vessel via said further outlet and the liquid withdrawn from the vessel via the outlet at the bottom of the vessel is substantially bubble-free.

The "ultrasonic wind" effect is not dependent on gravity and experiments have established that the apparatus of the invention, once operation has been established, will continue to operate with quite radical departures of the axis of rotational symmetry of the vessel from verticality, and even with such axis horizontal or with the apparatus inverted. However, because the most convenient starting conditions can generally only conveniently be obtained with said axis of rotational symmetry at least approximately vertical, the term "vertical" is used herein but it should be appreciated that it is not used in any strict sense.

BRIEF DESCRIPTION OF THE DRAWINGS

For a better understanding of the present invention, reference will now be made, by way of example only, to the accompanying drawings in which.

DETAILED DESCRIPTION OF THE INVENTION

Figure 2:
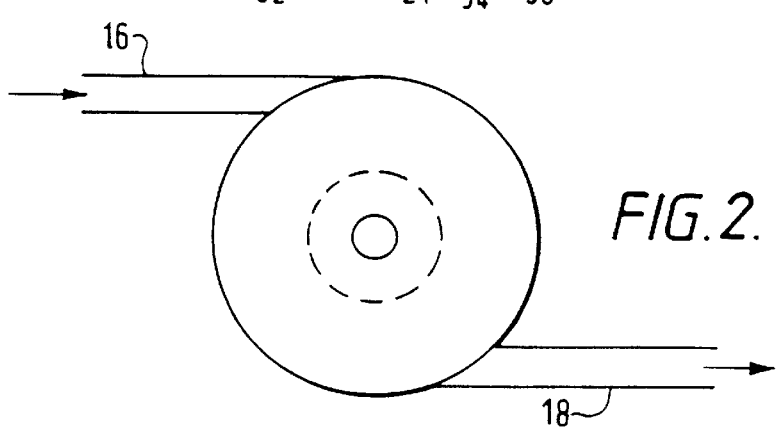
FIG. 2 is a schematic plan view of the apparatus of FIG. 1.

Referring to the drawings, the apparatus comprises a generally cylindrical vessel 10 arranged with its longitudinal axis vertical, the vessel being closed at the top and bottom by respective upper and lower end walls 12, 14. A horizontal inlet pipe or conduit 16 extends chordally and, in the arrangement shown in FIG. 2, substantially tangentially with respect to the cylindrical wall of the vessel and meets that wall in an inlet port. Thus, the longitudinal axis of the inlet conduit 16 is substantially offset laterally with respect to the vertical central axis of the vessel 10. A horizontal outlet conduit 18 extends from an outlet port at the bottom of the cylindrical wall of the vessel, the outlet conduit being likewise disposed chordally or tangentially with respect to the cylindrical vessel 10. It will be appreciated that, with the arrangement illustrated in FIG. 2, the supply of liquid to the vessel 10 via the inlet conduit 16 at any appreciable rate, will result in the liquid within the vessel having a spin imparted thereto which is clockwise about the vertical axis as viewed in FIG. 2. That is to say, given a net flow from the inlet 16 to outlet 18 through the vessel, the liquid proceeds in a spiralling movement from the upper to the lower end of the vessel. As illustrated, the disposition of the outlet conduit 18 with respect to the spin induced by the supply of liquid via the inlet conduit 16 is such that the liquid in the vessel in the region of the outlet port has a substantial component of motion along the axis of the outlet conduit in the direction of the discharge through the outlet conduit and thus tends to maintain the spin of liquid within the vessel. However, the orientation of outlet 18 is not of great importance and it may extend radially or in any other direction.

A device 19 is provided for propagating an ultrasonic beam axially within the vessel 10. The device comprises a transducer portion, indicated generally at 20, outside the vessel 10, below end wall 14 and an ultrasound-conducting and propagating member 22 of solid cylindrical form in the present embodiment but referred to herein, for convenience, as a "horn", extending axially within the vessel from the bottom end wall 14.

Figure 1:
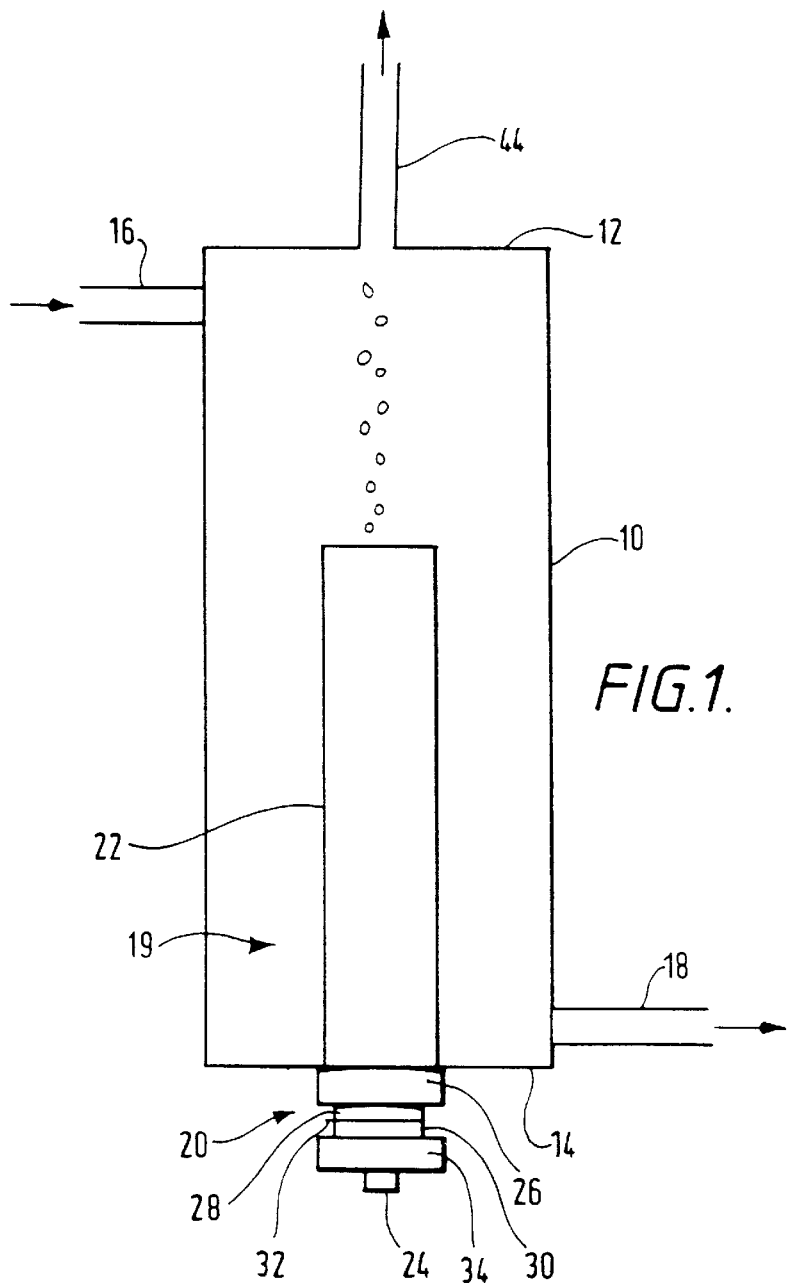
FIG. 1 is a schematic view partly in side elevation and partly in axial section of an apparatus embodying the invention.

The horn may, for example, comprise a cylindrical metal bar of predetermined length having a flat upper end face perpendicular to the common axis of horn 22 and vessel 10. The horn 22 has a screw-threaded axial passage (not shown) extending from its lower end and receiving a securing bolt 24 (the head of which is visible in FIG. 1), passed through a central hole in the lower end wall, and passing through an axial passage provided in the stack of components forming the transducer portion 20. The bottom end wall 14 is thus clamped, by the bolt 24, between the lower end face of the horn 22 and the transducer portion 20, whereby the aperture in the end wall 14 is sealed against passage of liquid or air and the device 19 is mechanically secured to the end wall 14.

The transducer 20 is based upon the Langevin sandwich, known per se and comprises a first annular end mass 26 below the lower end wall 14, a first annular piezo-electric crystal 28 below end mass 26, an annular contact plate 32 disposed between the crystal 28 and a second annular piezo electric crystal 30 matched with crystal 28 and a second annular end mass 34 disposed below crystal 30 and above the head of the bolt 24. The contact plate 32 is electrically connected with an ultrasonic signal generator (not shown) providing an a.c. electrical signal (e.g. of 40 kHz).

The horn 22 and the components of the transducer portion 20 are selected and dimensioned, in manner known per se, to afford efficient conversion of electrical energy supplied to the transducer portion 20 to ultrasonic energy propagated upwardly, axially in the vessel 10 from the flat upper end face of the horn 22, at the selected ultrasonic operating frequency of the device (preferably, as noted above, around 40 kHz). The end wall 14 is constructed as a flexible metal diaphragm to accommodate ultrasonic vibrations in the vertical sense imparted to the lower face of horn 22, and thus to the central portion of wall 14, by the transducer portion 20. A vent conduit 44 extends axially from a vent outlet located centrally in the top end wall 12 of the vessel.

In operation of the apparatus, liquid to be debubbled is supplied to the vessel via the inlet conduit 16 from a supply vessel (not shown) and liquid containing entrained air bubbles is drawn from the vessel via the vent conduit 44 and returned (recycled) to the supply vessel, whilst debubbled liquid is discharged from the outlet conduit 18.

In one embodiment of the invention, designed to operate at a frequency of 40 kHz, the vessel 10 may have an internal diameter of 7.5 cm and an axial length of 42.5 cm with a horn 22 of stainless steel of an axial length of 19 cm and diameter of 4 cm. The length of the vessel 10 is not critical, provided it is at least the length of the horn plus several wavelengths of the ultrasound in the liquid concerned.

The device is operated with a minimum pressure of 20.7 kPa (3 psi) in the vessel 10, but it has been found that the performance of the device, in terms of its capacity to debubble liquid with large amounts of entrained air at large liquid flow rates, improves with increased pressurisation, and pressures as high as 0.31 MPa (45 psi) have been employed successfully. The action of the ultrasonic energy propagated through the vessel above the upper end face of horn 22 is to break up any larger bubbles which may enter via inlet 16 and to propel the resulting smaller bubbles upwardly by virtue of the "ultrasonic wind" effect noted above.

The spiral movement of the liquid within the vessel 10 is all-important because it disciplines the bubble path. Experiments have established that without such spiral movement, (engendered in the preferred embodiment by the tangential entry of liquid into and exit of liquid from the vessel), a cloud of bubbles forms right across the cross section of the vessel and prevents the "wind" bubbles from the horn from escaping freely up and out of the vent 44. If this happens the device very quickly fails catastrophically because ultrasound will not transmit through a blanket of air bubbles.

The flow rate from the vessel 10 through the vent conduit 44 need simply be enough to carry away all the bubbles. With a device of the dimension exemplified above, a flow rate of 0.21/min to 11/min has been found to be more than adequate. The applicants have found that, for proper operation, the vessel 10 must, at start-up, be completely free of bubbles below the level of the upper end of the horn 22. Thus, start procedure is important. Where, as indicated above, the liquid with entrained bubbles extracted from the vessel 10 is recycled to the supply vessel, provision must be made for the removal of such bubbles before the liquid is returned to the vessel 10, for example by allowing time for such bubbles to separate from the liquid. In the absence of such provision the bubbles will return to the vessel 10 and eventually choke the system.

The apparatus described makes use of the so-called "wind", which is created by an ultrasonic transducer cavitating in a liquid, to propel bubbles to the top of the vessel 10, where the vent pipe 44 allows bubbles to be continuously removed. For the purpose required, the apparatus with its cylindrical vessel 10 and coaxial transducer, with a distance of several wavelengths (at 40 kHz in liquid) in front of the face of the "horn", appears to be the ideal design.

When operated correctly and within its limits, the apparatus described will let no bubbles at all pass downwardly past the upper end of the horn 22. Experiments have confirmed that the limiting factor in performance of the apparatus is when the liquid flow rate through it causes a linear downward liquid velocity which overpowers the upward velocity of the bubbles due to the ultrasonic "wind", so that bubbles reach the region between the wall of vessel 10 and the side of horn 22, below the upper end face of the horn. In practice, it has been found that the apparatus can handle surprisingly high flow rates (via inlet 16 and outlet 18) before this limiting condition is reached. It is believed that this is, at least in part, because higher flow rates produce faster swirl within the vessel and thus increased centrifugal force so that bubbles entering with the liquid via inlet 16 are more rapidly delivered to the region adjacent the axis of the vessel 10 where the effect of the "ultrasonic wind" and of the removal of liquid via outlet 44 are greatest and where any downward component of liquid velocity is least.

Besides its effectiveness in eliminating bubbles, the apparatus described has been found to be capable of debubbling liquid at flow rates which are substantially higher, in relation to the volume of the vessel 10, than known debubbling apparatus and yet with a power expenditure substantially less than known apparatus of comparable capacity. The low volume of the vessel is advantageous in photographic emulsion coating systems in particular, because such coating is carried out on a batch basis and it is necessary to wash out and purge such systems between batches and also when faults occur. The volume of any debubbling apparatus must be included in the volume of emulsion lost (i.e. rendered unusable without further processing or recycling) so that the small volume of the debubbling apparatus of the invention allows substantial savings to be effected.

Figure 3:
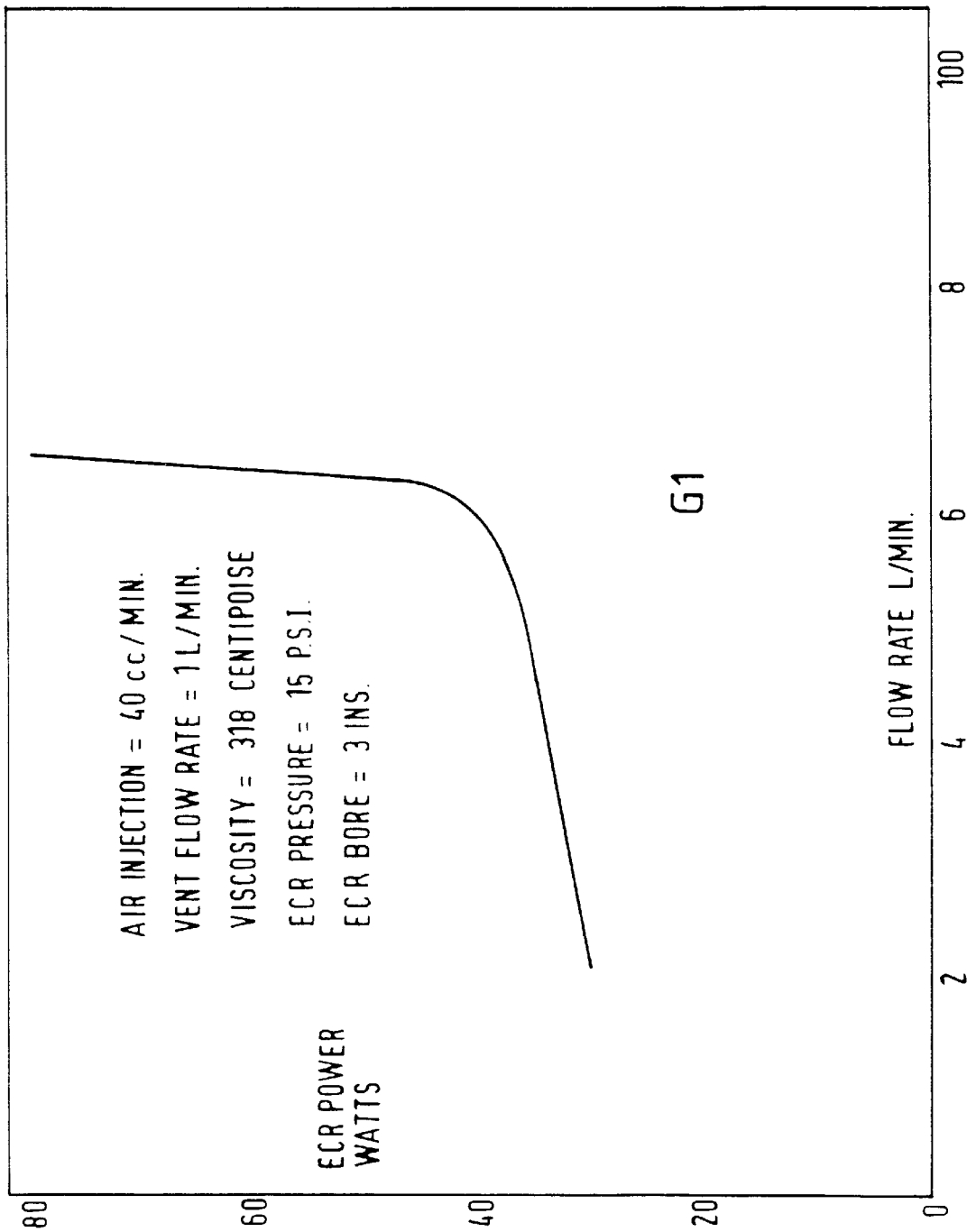
FIG. 3 is a graph of electrical power supplied against maximum working liquid flow rate for an embodiment of the invention.
Figure 4:
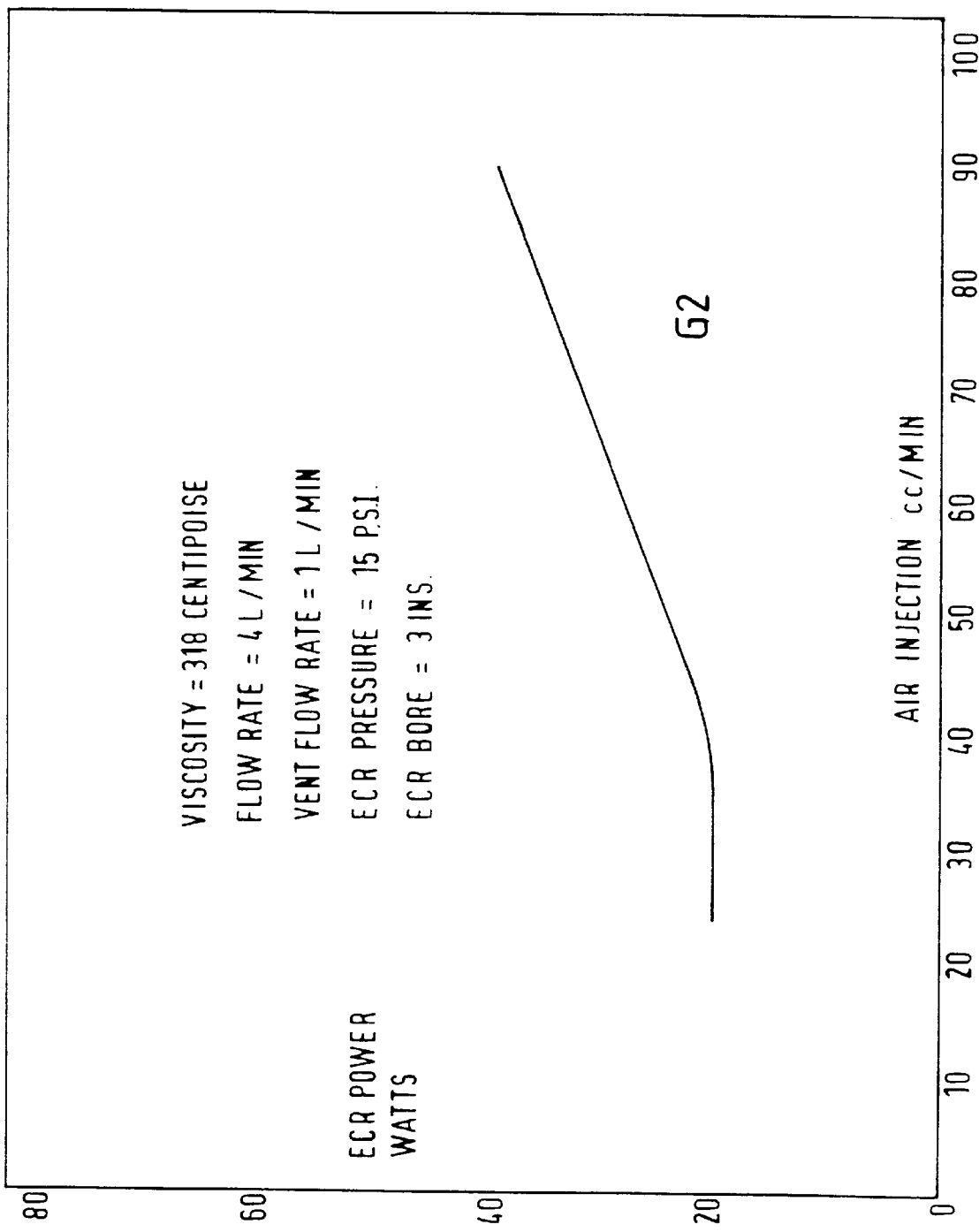
FIG. 4 is a graph of electrical power supplied against air entrainment for satisfactory operation of the same embodiment.
Figure 5:
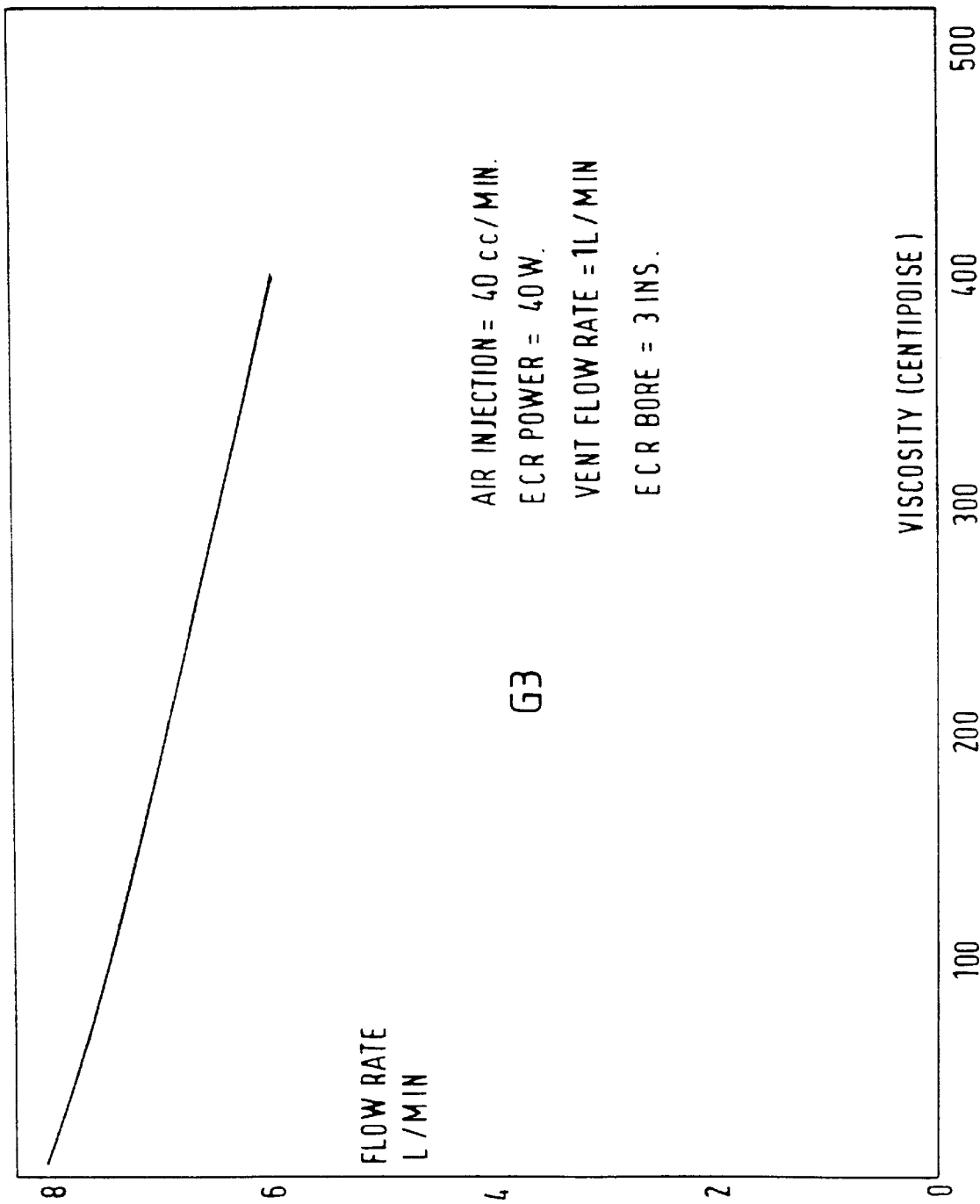
FIG. 5 is a graph of maximum working flow rate against viscosity for the same embodiment.

The three graphs of FIG. 3, FIG. 4 and FIG. 5 are a selection from a whole family of curves and show the working limit of the apparatus in each case. FIG. 3 shows how at a fixed viscosity and vessel pressure and air entrainment rate (air injection rate), the maximum working flow rate possible is virtually independent of power supplied to the transducer. FIG. 4 shows how for a given viscosity, flow rate and operating pressure, a certain minimum power is required for the apparatus to work and that more power is required with an increasing percentage of air entrainment. The minimum power required in FIG. 4 is the level at which cavitation starts in the solution of viscosity 318 centipoise being used in the test. For a viscosity of 10 centipoise, this minimum level drops to around 10 W. FIG. 5 shows how the maximum working flow rate varies only slightly with viscosity.

Whilst, in the preferred embodiment described with reference to the drawings, a further outlet 44 is provided at the upper end of the vessel, centred on the vertical longitudinal axis of the vessel, in some embodiments no such further outlet may be provided, the air in the bubbles propelled upwardly by the ultrasonic wind merely being allowed to accumulate in the upper end of the vessel. Such an arrangement is practicable in short batch production runs where the amount of air so accumulating in a single run will not be sufficient to reduce to dangerously low levels the depth of liquid above the horn 22. At the end of the production run, the accumulated air may be removed by reverse flow of liquid through the vessel and the connected parts of the system.

Likewise a further outlet for air need not be disposed on the axis of the vessel if some air space above the liquid in the vessel can be tolerated, but such further outlet, for removal of air without liquid, may extend from the peripheral wall of the vessel adjacent the upper end of the vessel.

Furthermore, it is not essential, in every case, to impart spin or a spiralling motion to liquid within the vessel, particularly if liquid flow rate and the amount of entrained air are small, since in such a case there may not be enough bubbles at any time to form a dense cloud which would impede transmission of the ultrasound.

As noted above, the longitudinal axis of the vessel need not be strictly vertical and, indeed, the starting and running requirement that there should be no bubbles in the region between the side of the horn and the side of the vessel can be met by an arrangement in which the axis of the vessel is inclined only slightly upwardly from the outlet end to the inlet end although in such an arrangement it is preferred that the inlet port should be lowermost.

The vessel 10 need not be in the form of a straight cylinder but may, for example, diverge conically from its upper end or may comprise an upper cylindrical section of smaller diameter, an intermediate downwardly diverging section and a lower cylindrical section of greater diameter, for example extending over the length of the horn. The last noted arrangement may be useful in counteracting the restriction of the flow cross-section of the vessel caused by the presence of the horn, and which, by reducing pressure, may tend to produce bubbles in the region between the side of the horn and the wall of the vessel by bringing air out of solution.

In general, the flow capacity of the apparatus may be increased by increasing the diameter, but such increase, which may also necessitate an increase in height in order to ensure that the ultrasonic beam fills the cross-section of the vessel over an adequate column of the liquid so that there is a liquid wastage penalty attached to such increase in flow capacity, at least where the apparatus is used for de-bubbling photographic emulsion.

We claim:

1. A debubbling apparatus comprising:
   (a) a vessel operating at a pressure of at least about 3 psi, said vessel having a liquid inlet through which a liquid is introduced, a first liquid outlet and a second liquid outlet, said liquid inlet being positioned proximate to a first end of said vessel and said first liquid outlet being positioned proximate to a second end of said vessel, said liquid inlet angled to cause liquid introduced therethrough into said vessel to travel a spiral path through said vessel toward said first liquid outlet;
   (b) an ultrasonic horn extending into said vessel from said second end, said ultrasonic horn terminating at an upper face which is short of said first end and said liquid inlet, said ultrasonic horn transmitting ultrasonic energy along a longitudinal axis of said vessel toward said second liquid outlet driving air bubbles entrained in the liquid toward said second outlet; and
   (c) a liquid stream drawn through said second liquid outlet containing air bubbles entrained therein.

2. A debubbling apparatus as recited in claim 1 wherein: said ultrasonic horn operates at a predetermined frequency.

3. A debubbling apparatus as recited in claim 2 wherein: said predetermined frequency is about 40 kHz.

4. A debubbling apparatus as recited in claim 1 wherein: said vessel is cylindrically shaped.

5. A debubbling apparatus as recited in claim 1 wherein: said vessel is conically shaped.

6. A debubbling apparatus as recited in claim 2 wherein: said upper face is spaced apart from said upper end by a distance of at least several wavelengths.

7. A debubbling apparatus as recited in claim 1 wherein: said ultrasonic horn creates an ultrasonic wind effect allowing said debubbling apparatus to function in any orientation.

8. A method for debubbling a liquid comprising the steps of:
   (a) introducing the liquid to a vessel through an inlet located proximate to a first end of the vessel;
   (b) causing the liquid to flow through the vessel in a spiral path toward a first outlet positioned proximate to a second end of the vessel;
   (c) operating an ultrasonic horn within the vessel to transmit an ultrasonic wave from an upper surface of the ultrasonic horn along a longitudinal axis the vessel toward the first end and toward a second outlet;
   (d) operating the vessel at a pressure of at least about 3 psi;
   (e) withdrawing a bubble-free stream of liquid through the first outlet;

(f) withdrawing a stream of liquid containing entrained air bubbles through the second outlet.

9. A method as recited in claim 8 wherein:

said first operating step generates an ultrasonic wind effect sweeping bubbles way from an internal surface of the vessel and along an axial path toward the second outlet.

10. A method as recited in claim 9 further comprising the step of:

operating the ultrasonic horn at a predetermined frequency.

11. A method as recited in claim 10 wherein:

said predetermined frequency is about 40 kHz.

12. A debubbling apparatus as recited in claim 10 wherein:

said ultrasonic horn includes a circumferential surface which is spaced apart from an internal surface of said vessel by a distance of about one wavelength.

* * * * *